United States Patent [19]

Coutoumanos

[11] Patent Number: 5,586,976
[45] Date of Patent: Dec. 24, 1996

[54] MEDICAL SYRINGE NEEDLE SHEATH HOLDING DEVICE

[76] Inventor: Vincent M. Coutoumanos, 8512 Steeple Ridge, North Richland Hills, Tex. 76180

[21] Appl. No.: 540,962

[22] Filed: Oct. 11, 1995

[51] Int. Cl.[6] ................................ A61M 5/00
[52] U.S. Cl. .................. 604/192; 604/263; 128/919
[58] Field of Search .................. 604/192, 187, 604/110, 263; 128/919; 206/364–366

[56] References Cited

U.S. PATENT DOCUMENTS

| | | | |
|---|---|---|---|
| 4,311,138 | 1/1982 | Sugarman. | |
| 4,356,822 | 11/1982 | Winstead-Hall. | |
| 4,573,976 | 3/1986 | Sampson et al. | 604/198 |
| 4,631,057 | 12/1986 | Mitchell | 604/198 |
| 4,923,447 | 5/1990 | Morgan | 604/198 |
| 4,986,816 | 1/1991 | Steiner et al. | 604/263 X |
| 4,995,871 | 2/1991 | Sasaki et al. | 604/110 |
| 5,024,666 | 6/1991 | Pituch | 604/263 |
| 5,160,324 | 11/1992 | Halbach | 604/192 |
| 5,209,738 | 5/1993 | Bruno | 604/192 |
| 5,242,426 | 9/1993 | Pituch | 604/263 |
| 5,279,577 | 1/1994 | Collett | 604/192 |
| 5,279,578 | 1/1994 | Cooke | 604/192 |
| 5,300,028 | 4/1994 | Welcheck | 604/192 X |

*Primary Examiner*—John D. Yasko
*Attorney, Agent, or Firm*—D. Scott Sudderth, Esq.

[57] ABSTRACT

A medical syringe needle sheath holding device (10) for use in uncapping and recapping a needle sheath over a needle of a medical syringe, which is portable and easy to use. The holding device (10) includes a holder body (16) having a sheath receiving passage (21) formed therethrough. A plunger (35) projects from one end of the holder body (16) and includes a sheath receiving aperture (39) formed therein. As the plunger is depressed, the sheath receiving aperture (39) of the plunger (35) is aligned with the sheath receiving passage (21) of the holder body. (16) to enable the needle sheath to be inserted therein. As the plunger (35) is released, it is urged rearwardly along the holder body (16) by a spring (42) so that the needle sheath is engaged and held between the plunger (35) and the holder body (16).

9 Claims, 3 Drawing Sheets

MEDICAL SYRINGE NEEDLE SHEATH HOLDING DEVICE

FIELD OF THE INVENTION

The present invention relates in general to safety devices for holding a protective sheath of a needle for a medical syringe. In particular, the present invention relates to a portable and simple to use safety device for removing and holding the protective sheath of a medical syringe needle during use and for recapping the needle, so as to minimize the risk of contact between the needle and the user to avoid accidental stabbing of the user with the needle.

BACKGROUND OF THE INVENTION

In recent years, a primary focus and concern of the medical profession has been on increasing safety procedures and minimizing the health risks to medical workers. Doctors, nurses, laboratory researchers and other medical care personnel are facing new and increasingly significant health risks every day. For example, AIDS and other deadly and incurable diseases not known twenty years ago are at the forefront of medical treatment problems today. There is, however, much about these diseases that is not known to the medical community, such as all of the various ways by which these diseases can be transmitted and, as in the case of AIDS, how to cure the disease. It therefore is critical that the contact between medical personnel and contaminated materials, i.e., needles, etc., be minimized as much as possible to minimize the health risks to which such workers are exposed.

One of the most significant dangers of transmission of disease and contaminants for medical personnel arises from the use of needles, such as in drawing blood and administering injections. When handling needles, there is always a possibility of the worker being accidentally stuck or stabbed by the needle. Recently, stores of medical workers being accidentally stabbed by contaminated needles and contracting life threatening diseases such as HIV, the virus that causes AIDS, have become all too frequent an occurrence. Often, such accidental contact occurs when the medical worker attempts to replace a protective plastic sheath over the needle. Such protective sheaths generally comprise thin plastic tubes adapted to fit over the needle to prevent contact with the needle.

Herefore, when replacing the protective sheath over a needle, the worker has had to hold the sheath in one hand while inserting the needle therein with their other hand. Accordingly, the worker must exercise extreme care in inserting the needle into the sheath. Even a slight slip or mistake can lead to the worker being stuck by the needle. As activity about the worker increases and the worker becomes stressed, fatigued or distracted, the chances of an accidental stabbing of the worker by a needle significantly increase.

In light of these increasing safety concerns for on medical and health care personnel, attempts have been made to develop devices to minimize the potential for contact between a worker or the person handling a syringe and the needle of the syringe. For example, U.S. Pat. No. 5,279,577 of Collett discloses a device that is adapted to be mounted to a shelf, about a pole or on a wall in a room. The device has a rest or bracket having a substantially U-shaped opening in which the needle sheath is received and is engaged for removing the sheath from the needle. Similarly, U.S. Pat. No. 5,242,426 of Pituch and U.S. Pat. No. 5,209,738 of Bruno both disclose stand alone containers or holders in which the sheath for a needle is received and engaged for removing the needle from the sheath. The problem with such devices is that they often are inconvenient to use. Additionally, these devices can be somewhat costly and generally are not portable so that medical care personnel can carry these devices with them for use when and where needed.

Other attempts to guard a needle from contact with the worker handling a syringe have focused on the development of syringe assemblies having shields or guards that are spring-loaded or adapted to otherwise move over the needle to cover the needle when not in use, such as disclosed in U.S. Pat. Nos. 4,923,447, 4,631,057 and 4,573,976. Such needle shields or covers are, however, expensive to manufacture, especially when considered in terms of the relatively low cost and disposable nature of syringes. Additionally, such protective devices are difficult to manufacture and difficult to use. Thus, while such devices provide enhanced protection against accidental stabbing of medical care personnel by needles when handling a syringe, the cost and difficulty of using such protective cover assemblies unfortunately has severely limited their use.

Accordingly, it can be seen that a need exists for a portable, hand-held medical safety device for removing and replacing the needle within a protective shield for a syringe which is inexpensive to produce and simple and easy to use.

SUMMARY OF THE INVENTION

Briefly described, the present invention comprises a medical syringe needle sheath holding device for removing, holding and replacing a protective needle sheath for a needle of a syringe. The holding device generally is designed to be a portable, hand-held device to be carried by medical care personnel and is designed to minimize the contact between medical care personnel and needles of the syringes as the protective sheath is removed therefrom and replaced over the needle after use.

The needle sheath holding device generally includes a substantially tubularly shaped holder body having a first end and a second end. A sheath receiving passage is formed through the holder body at a position intermediate the first and second ends of the holder body. The sheath receiving passage has a diameter substantially larger than the diameter of the needle sheath for ease in receiving the needle sheath therethrough. The holder body further includes a battery compartment formed adjacent the first end thereof and an open-ended rear channel formed between the second end of the holder body and the battery compartment.

A means for engaging and holding the needle sheath within the sheath receiving passage is received and is movable along the length of the rear channel of the holder body. The means for engaging and holding the sheath generally comprises a plunger having a pointed first end and a substantially flat rear or second end, and includes a sheath receiving aperture formed adjacent the pointed first end thereof. A compression spring or similar means for biasing the plunger along the rear channel of the holder body is attached about the plunger adjacent the rear end thereof. The spring tends to bias the plunger rearwardly toward the rear end of the holder body.

An actuator button is inserted into the open second end of the holder body and engages the flat rear end of the plunger. Thus, as the button is depressed, the plunger is urged forwardly along the length of the holder body to move the sheath receiving aperture of the plunger into alignment with the sheath receiving passage of the holder body. The needle sheath is enabled to be inserted through the holder body. Thereafter, the actuator button is released by the user, causing the plunger to be biased rearwardly along the length of the holder body by the spring. As a result, the needle sheath is caught and held between the plunger and the holder body. The user thereafter simply slides the needle out of its protective sheath for use of the syringe.

After use, the user simply guides the needle back into the needle sheath without physically contacting the needle sheath. Thus, the chances of an accidental stabbing or contact between the user and the how contaminated needle of the syringe are minimized. After the needle has been reinserted into the sheath, the actuator button again is depressed, causing the plunger to be moved forwardly along the holder body. The protective needle sheath thereby is released from engagement between the plunger and holder body. The syringe thereafter should be disposed of in a proper disposal means.

A light or similar illuminating mechanism is mounted in the first end of the holder body and is actuatable by the engagement and depression of the plunger. The light includes a battery or similar power means mounted in the battery compartment formed adjacent the first end of the holder body. A light bulb is mounted in contact with the battery, and a trigger means is positioned within the battery compartment and is adapted to be engaged by the pointed first end of the plunger upon the movement of the plunger along the holder body. As the actuator button, and thus the plunger, is depressed and moved along the holder body, the pointed first end of the plunger urges the trigger into engagement with the negative pole of the battery. This completes the circuit between the light bulb and the battery to power and thus illuminate the light bulb. The present invention thus can perform the dual functions of a safety device for removing, holding and replacing a protective sheath of a needle of a syringe to minimize the potential for contact and accidental stabbing of health care workers by contaminated needles, and at the same, providing a easy to carry and use penlight as generally required and used by medical care personnel.

Various objects, features and advantages of the present invention will become apparent to one of ordinary skill in the art upon reading the following specification, taken in conjunction with the accompanying drawings.

DETAILED DESCRIPTION

Figure 1:
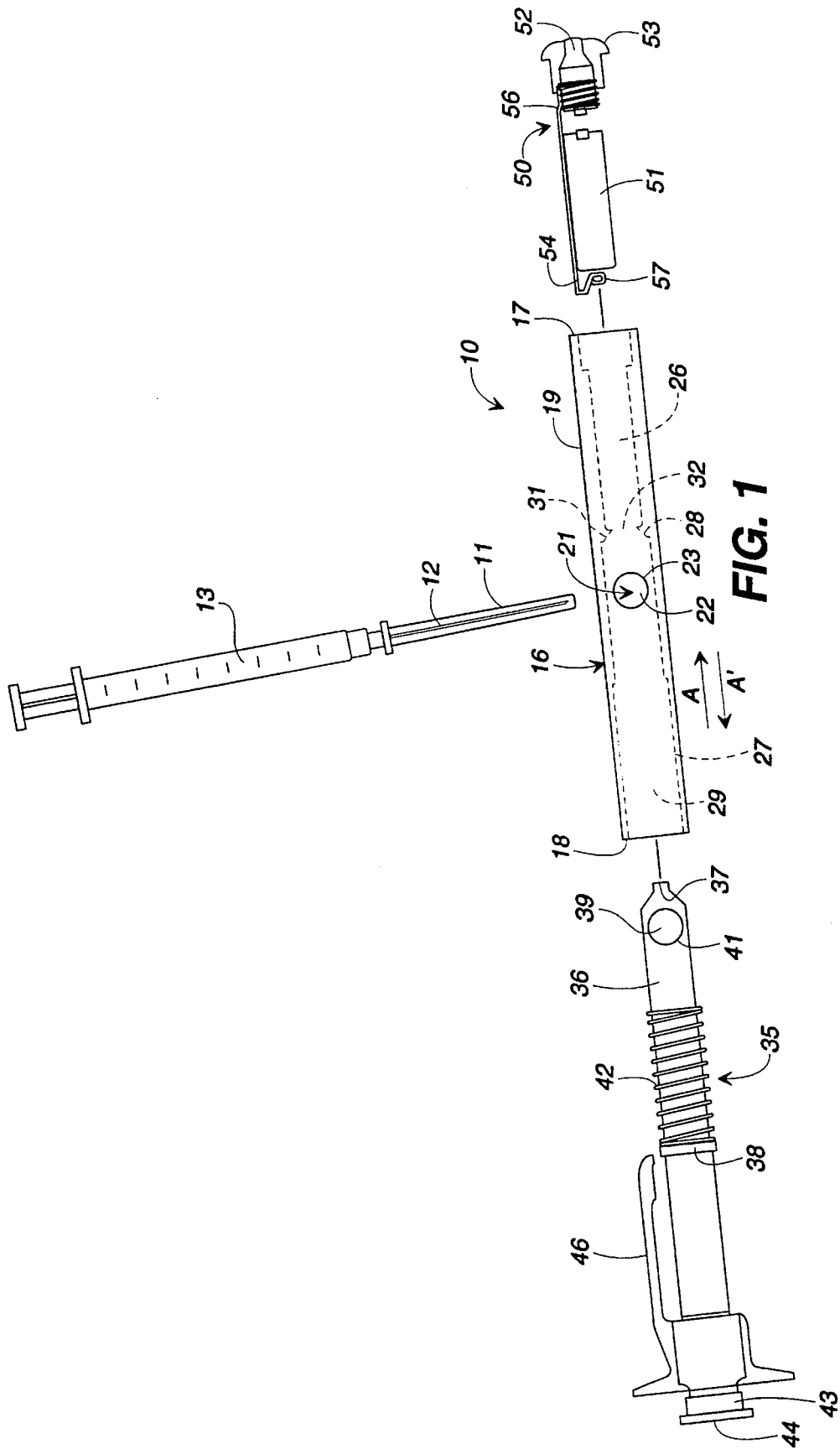
FIG. 1 is an exploded perspective view of the medical syringe needle sheath holding device, illustrating the various components thereof and a syringe having a protective sheath over its needle.

Referring now in greater detail to the drawings in which like numerals indicate like parts throughout the several views, FIG. 1 illustrates the medical syringe needle sheath holding device 10 for removing, holding and replacing a protective plastic needle sheath 11 received over a needle 12 of a syringe 13. The syringe is generally is a conventional needle syringe as commonly used for administering medicines, drawing blood, etc., and having a needle capped or sheathed with the plastic needle sheath 11.

Figure 2:
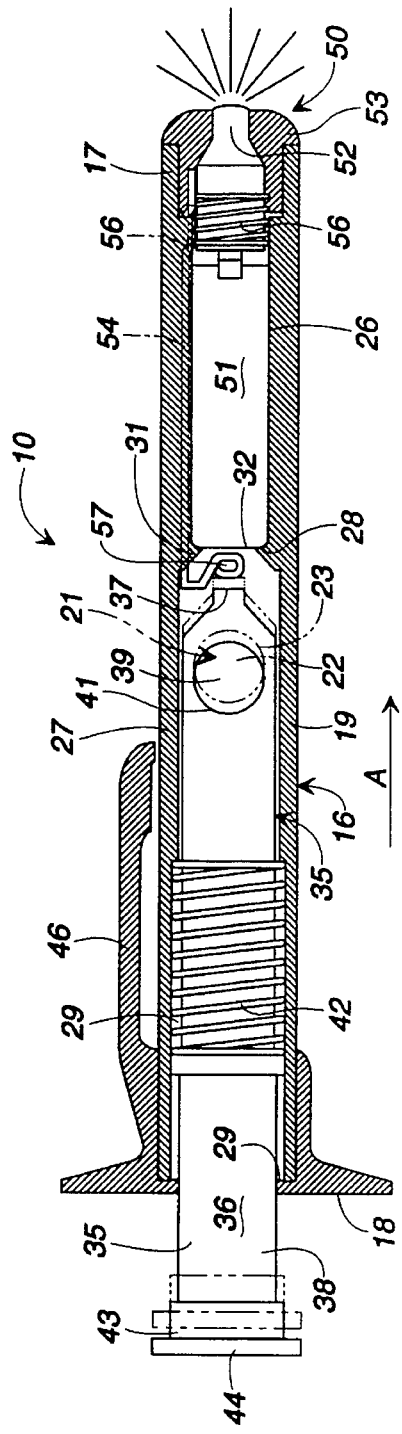
FIG. 2 is a side elevational view taken in cross section, illustrating the components of the medical syringe needle sheath holding device.

As illustrated in FIGS. 1 and 2, the holding device 10 includes a holder body 16, which generally is an elongated substantially tubularly-shaped member having a first or front end 17, a second or rear end 18 and a cylindrical sidewall 19. The holder body typically is formed from a plastic material, although it also can be formed from metal or other resilient, light-weight materials. A sheath receiving passage 21 is formed through the holder body 16 intermediate the first and second ends thereof. The sheath receiving passage includes substantially circularly-shaped apertures or opening 22 (FIG. 2) formed in the sidewall 19 of the holder body. The apertures 22 are aligned with one another and each includes a circular sidewall 23. The diameter of the sheath receiving passage is substantially greater than that of the needle sheath 11 (FIG. 1) to facilitate the easy insertion and removal of the needle sheath from the sheath receiving passage.

Figure 3:
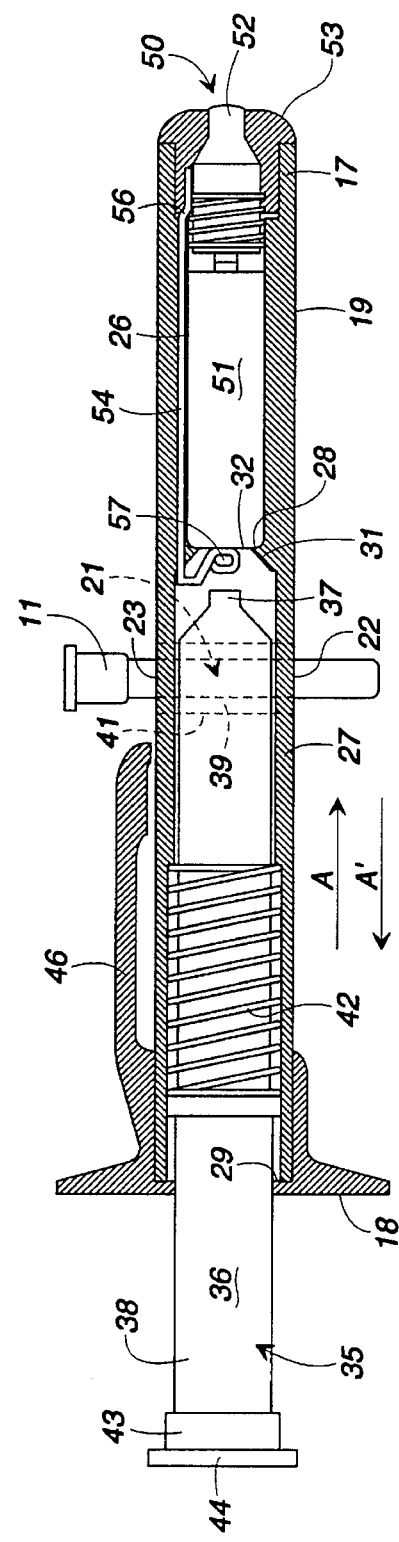
FIG. 3 is a side elevational view taken in cross section, illustrating the engagement of the protective needle sheath of the syringe by the medical syringe needle sheath holding device.

As illustrated in FIGS. 1, 2 and 3, the holder body generally is hollow and includes a battery compartment 26 formed adjacent the first or front end 17 of the holder body 16, and a rear channel or passage 27 extending from the second or rear end 18 of the holder body to the rear end 28 of the battery compartment 26. The rear channel 27 is substantially cylindrically shaped, having an open proximal or rear end 29 and a front or distal end 31 that tapers toward the rear end 28 of the battery compartment 26. A tapered opening 32 is formed between the front end 31 of the rear channel 27 and the rear end 28 of the battery compartment 26, as illustrated in FIGS. 1 and 3.

As shown in FIGS. 1, 2 and 3, a plunger 35 is received within and is movable along the length of the rear channel 27 of the holder body 16 in the direction of the arrows A and A'. The plunger is formed with a substantially tubularly shaped body 36 having a tapered, pointed front engaging end 37 and a substantially flat rear end 38. A sheath receiving aperture 39 is formed through the body 36 of the plunger adjacent the front, engaging end 37 thereof. The aperture is circularly shaped with a circular sidewall 41. The aperture is adapted to be aligned with the sheath receiving passage 21 (FIGS. 1 and 2) of the holder body when the plunger is moved in the direction of the arrow A for receiving the needle sheath 11 (FIGS. 1 and 3) therethrough.

A compression spring or similar biasing means is mounted about the body 36 of the plunger 35 adjacent the rear end 38 thereof. The compression spring engages the sidewall of the rear channel 27 of the holder body and urges the plunger 35 in the direction of arrow A' toward a rearward, resting position when not in use. Additionally, when a needle sheath 11 is received through the sheath receiving passage of the holder body and through the aperture of the plunger, the movement of the plunger rearwardly in the direction of arrow A' due to the spring 42 causes the needle sheath to be engaged between the sidewall 41 of the aperture 39 of the plunger and the sidewall or edge 23 of apertures 22 of the holder body 16, as illustrated in FIG. 3. The plunger thus functions as a means for engaging and holding the needle sheath within the holder body for removing and replacing the needle of a syringe within its needle sheath.

An actuator button 43 is positioned at the second end 18 of the holder body 16. As illustrated in FIGS. 2 and 3, the actuator button 43 projects into the open second end 18 of the holder body and engages the rear end 38 of the plunger body. The actuator button further includes a wide, flattened surface 44 adapted to be engaged by a finger or thumb of a user during use of the holding device 10. When the actuator button is depressed, the plunger 35 is urged in the direction of arrow A along the length of the rear channel of the holder body so as to move the sheath receiving aperture 39 of the plunger into alignment with the apertures 22 of the sheath receiving passage formed through the holder body.

A clip 46 additionally is provided for clipping the holding device 10 to a clipboard, shirt pocket, etc., for easy access and convenience by a user. Finger grips (not shown) also can be provided adjacent the rear end of the holder body for ease of gripping the holder body as the actuator button is engaged.

A light means or illuminating mechanism 50 is mounted in the first end 17 of the holder body 16 of the holding device 10. The light includes a battery 61, or other power source, which is mounted within the battery compartment 26 of the holder body. As indicated in FIGS. 1 and 2, the negative pole of the battery is received at the rear end 28 of the battery compartment, covering the opening 32 formed between the battery compartment and the rear channel of the holder body. The battery typically is a AA or AAA size 1.5 volt battery, although other batteries can be used depending on size constrains of the holder device. A light bulb 52 is positioned at the first end 17 of the holder body, in contact with the positive pole of the battery 51. An end cap 53 is received over the light bulb and attaches to the front end of the holder body to secure the light bulb within the holder body in contact with the battery.

As illustrated in FIG. 2, a trigger 54 is positioned within the holder body, extending along the length of the battery compartment 26. The trigger is an elongated strip of metal such as steel or cooper to conduct electrical current between the battery and the light bulb. The trigger includes a flat proximal end 56 that engages the light bulb at the front of the holder body, and a curled distal end 57 that extends downwardly adjacent the front end 31 of the rear channel 27 and is aligned with the opening 32 between the rear channel and battery compartment. As the plunger 35 is urged in the direction of arrow A upon depression of the actuator button 43, the pointed engaging end 37 of the plunger engages and urges the distal end 57 of the trigger 54 into contact with the negative pole of the battery. As a result, a circuit is completed to eliminate the light bulb.

Figure 4:
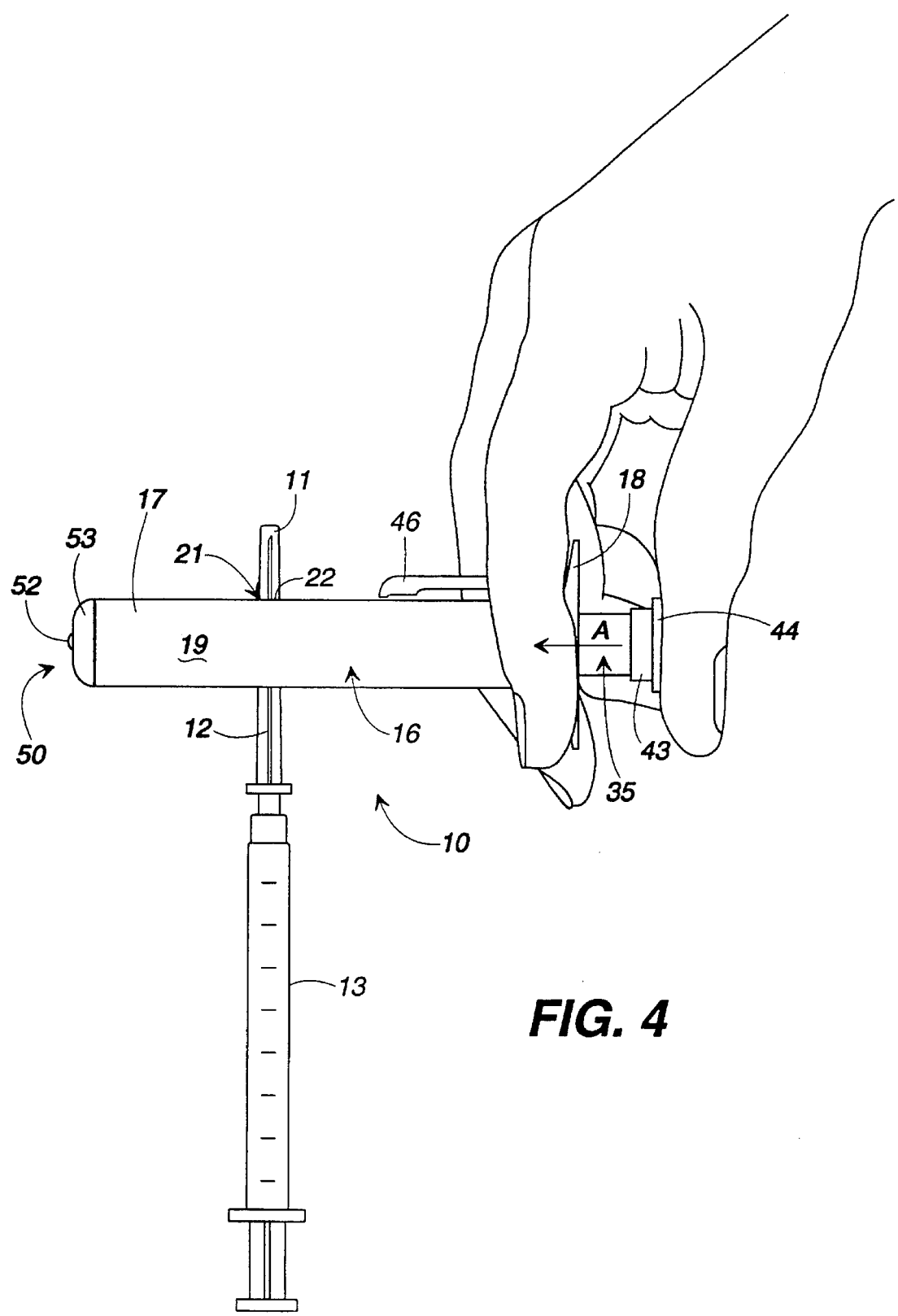
FIG. 4 is a side elevational view showing the operation of the medical needle sheath holding device to grip and hold a protective sheath of a needle syringe.

In operation of the medical syringe needle sheath holding device 10 (FIGS. 1–4), for holding a protective needle sheath for removal and replacement of the needle therein, as illustrated in FIG. 4, the user grasps the holder body 16 of the holding device 10 with the fingers positioned about the flange rear end 18 of the holder body. The user thereafter depresses the actuator button 43 to urge the plunger 35 in the direction of arrow A. As the plunger 35 is moved in the direction of arrow A, as illustrated in FIG. 2, the sheath receiving aperture 39 of the plunger is moved into alignment with the apertures 22 of the sheath receiving passage 21 of the holder body 16. With the apertures of the plunger and sheath receiving passage thus aligned, the protective needle sheath 11 (FIG. 3) can be inserted through the sheath receiving passage. The user thereafter releases the actuator button, in response to which the spring 42 urges the plunger rearwardly in the direction of arrow A' causing the needle sheath to be engaged and held between the sidewalls 23 of the apertures 22 and the sidewall 41 of the sheath receiving aperture 39. The syringe needle thereafter is removed from the sheath for use.

After use, the user simply guides the needle of the syringe back into its protective needle sheath. Thereafter, the user again depresses the actuator button in the direction of arrow A, as illustrated in FIG. 4, causing the plunger to be moved in the direction of arrow A to release the sheath from engagement between the sidewalls of the apertures of the sheath receiving passage and the sidewall of the sheath receiving aperture of the plunger. With the needle sheath thus released, the sheath is retracted from the holding device with the sheath covering the needle of the syringe. The syringe thereafter should be disposed of in a proper manner according to health regulations.

Additionally, the holding device 10 further can be used as a penlight or flashlight for use in physical examinations by medical care personnel. In such use, the user simply depresses the actuator button 43, causing the plunger to be moved in the direction of arrow A (FIG. 2) into contact with the curled distal end 57 of the trigger 54. The distal end of the trigger is pressed into engagement with the battery to complete the circuit between the battery 51 and the light bulb of the light means 50 to illuminate the light bulb. The end cap 53 further is preferably releasably attached to the first or front end of the holder body so as to enable removal and replacement of the light bulb and battery as needed or desired.

The present invention thus advantageously performs the dual functions of a portable, hand-held needle sheath holding device that enables a medical care worker to remove, hold and replace a protective sheath about the needle of a syringe, and providing a light for use by medical care personnel during physical examinations.

It will be understood by those skilled in the art that while the invention has been described above in reference to a preferred embodiment, various additions, deletions and modifications may be made to the present invention without departing from the spirit and scope of the invention as set forth in the following claims.

I claim:

1. A portable, hand-held pocket safety device for removing and replacing a needle sheath for the needle of a syringe with the risk of contact with the needle minimized, comprising:

a holder body having a sheath receiving passage formed therethrough;

a plunger means received within said holder body and movable through said holder body, said plunger means including an aperture formed therealong and adapted to be alignable with said sheath receiving passage of said holder body as said plunger means is moved along said holder body; and means for automatically biasing said plunger means along said holder body so as to move said aperture of said plunger means away from alignment with said sheath receiving passage upon release of said plunger means, such that said plunger means engages and holds a needle sheath received through said sheath receiving passage.

2. A portable, hand-held safety device for removing and replacing a needle sheath for the needle of a syringe with the risk of contact with the needle minimized, comprising:

a holder body having a sheath receiving passage formed therethrough;

a plunger means received within said holder body and movable along the length thereof, said plunger means including an aperture formed therealong and adapted to be alignable with said sheath receiving passage of said holder body as said plunger means is moved along said holder body;

means for biasing said plunger means along said holder body such that said plunger means engages and holds a needle sheath received through said sheath receiving passage; and light means mounted in a first end of said holder body and actuatable with the movement of said plunger means along said holder body.

3. The safety device of claim 2, and wherein said means for biasing comprises a compression spring mounted within said holder body about said plunger means and adapted to be engaged between said plunger means and said holder body as said plunger means is moved along said holder body and urges said plunger means rearwardly along said holder body so as to engage and hold a needle sheath within said sheath receiving passage between said plunger means and said holder body for removal and replacement of the needle sheet from a need.

4. The safety device of claim 2 and wherein said light means includes a light bulb mounted in said first end of said holder body, power means positioned adjacent said light bulb, and a trigger means positioned in contact with said light bulb and adapted to be engaged and move into contact with said power means with the movement of said plunger means forwardly along said holder body to connect said light bulb to said power means.

5. A portable, hand-held medical safety device for removing, holding and replacing a protective sheath for a needle of a syringe to minimize contact between the needle and a user, comprising:

a holder body sized and configured so as to readily fit within a hand of a user and having a first end, a second end, and a sheath receiving passage formed therethrough intermediate said first and second ends;

means for engaging and holding the sheath within said sheath receiving passage positioned along said holder body; and light means mounted at said first end of said holder body and selectively actuatable;

whereby the protective sheaths of a needle is received through said sheath receiving passage and held therein as the needle is removed from the sheath and as the needle is placed within the needle sheath without requiring contact between the user and the needle to remove and replace the needle sheath.

6. The hand-held safety device of claim 5 and wherein said light means comprises a light bulb mounted in said first end of said holder body, power means positioned adjacent said light bulb, and a trigger means positioned in contact with said light bulb and adapted to be engaged and move into contact with said power means with the movement of said plunger means forwardly along said holder body to connect said light bulb to said power means.

7. The hand-held safety device of claim 5 and wherein said means for engaging and holding the sheath comprises a plunger means positioned within and movable along said holder body and having a sheath opening formed therethrough, said sheath opening being aligned with said sheath receiving passage as said plunger means is moved along said holder body for receiving the sheath therethrough and holding the sheath in engagement between said plunger means and said holder body.

8. The hand-held safety device of claim 7 and further including means for biasing said plunger means along said holder body to cause the sheaths to be engaged along said holder body to cause the sheath to be engaged and held between said sheath receiving passage and said sheath opening.

9. The hand-held safety device of claim 5 and wherein said holder body is formed as a pen-light.

* * * * *